United States Patent [19]

Vinogradov et al.

[11] 4,144,748
[45] Mar. 20, 1979

[54] DEVICE FOR DETERMINING COEFFICIENT OF ADHESION OF PNEUMATIC WHEEL TIRES OF TRANSPORT VEHICLES TO ROAD PAVEMENT

[75] Inventors: Alexandr P. Vinogradov; Mikhail A. Pechersky, both of Moscow, U.S.S.R.; Andrei S. Tkachenko, deceased, late of Moscow, U.S.S.R., by Nadezhda A. Tkachenko, administrator

[73] Assignee: Gosudarstvenny Proektno-Izyskatelsky i Nauchno-Issledovatelsky Institut "Aeroproekt", Moscow, U.S.S.R.

[21] Appl. No.: 845,678

[22] Filed: Oct. 26, 1977

[51] Int. Cl.² .......................................... G01N 19/02
[52] U.S. Cl. .......................................... 73/146; 73/9
[58] Field of Search .................................. 73/146, 9, 8

[56] References Cited

U.S. PATENT DOCUMENTS 4,050,290  9/1977  Lonnroth ..................................... 73/9

FOREIGN PATENT DOCUMENTS 1269334  4/1970  United Kingdom ............................ 73/9

Primary Examiner—Donald O. Woodiel
Attorney, Agent, or Firm—Fleit & Jacobson

[57] ABSTRACT

The present invention relates to measuring techniques intended to determine the operational characteristics of a road pavement by assessing the braking conditions of transport vehicles. The device comprises a single-axle trailer whose frame is coupled by a tow pole to a towing vehicle. The trailer has only two wheels adapted for rotating on the moving trailer with longitudinal slipping in opposite directions. The device also comprises a recording instrument with a sensitive element which is located between the trailer frame and the free end of the pole and is kinematically linked therewith in such a manner that on the moving trailer the sensitive element is acted upon by a force which is proportional in magnitude to the sum of absolute values of the longitudinal traction forces acting on the wheels and is directed essentially parallel to the forces. Such a device will allow measuring the coefficient of adhesion with a maximum possible accuracy as compared with the prior art devices; in addition, it is quite simple in design and operation which ensures its successful and efficient employment on airfields.

3 Claims, 6 Drawing Figures

DEVICE FOR DETERMINING COEFFICIENT OF ADHESION OF PNEUMATIC WHEEL TIRES OF TRANSPORT VEHICLES TO ROAD PAVEMENT

The present invention relates to measuring techniques designed for determining the operational characteristics of road pavement by assessing the braking conditions of transport vehicles and more particularly it relates to a device for determining the coefficient of adhesion of the pneumatic wheel tyres of transport vehicles to the road pavement.

Most successfully the present invention can be utilized on airfields for estimating the braking conditions of aircraft on runways.

It is an established fact that the ability of a pneumatic wheel carrying a normal load to receive or transmit tangential forces when interacting with the surface of the road pavement is one of its essential properties enabling the transport vehicles to move and be braked. Good adhesion of the pneumatic wheel tyre to the surface of the road pavement improves reliability and safety of traffic.

The adhesion of the pneumatic wheel to the road pavement is habitually assessed by a coefficient of adhesion which is equal to the ratio of the tangential reaction or longitudinal traction force in the wheel-to-road contact zone to the normal reaction or normal load acting on the wheel. The coefficient of adhesion depends on a great variety of factors of which the fundamental ones are the type and condition of the road pavement, construction and material of the pneumatic tyre, tyre pressure, wheel loading, speed of the vehicle, temperature conditions, the percentage of wheel slipping or skidding. The effect of these factors, except the percentage of slipping, is taken into account while projecting roads, airfields and designing the wheels of motor vehicles and aircraft.

The percentage of slipping of a moving wheel depends not only on the design of the wheel and its drive but also on the individual abilities and professional skill of the driver or pilot.

The studies of the influence exerted by the percentage of wheel slipping on the value of the adhesion coefficient have shown that the maximum coefficient of adhesion is attained when the wheel moves not with 100% slipping (skidding) but with longitudinal slipping amounting to 10-20%.

It has been proved that the coefficient of adhesion of the wheel at 100% slippping on various kinds of the road pavement is 5-20% lower than the maximum coefficient of adhesion.

In view of the above, if it is desired to obtain a maximum adhesion of aircraft wheels to the airfield pavement in the course of braking, the braking systems of the modern aircraft provide for longitudinal slipping of the wheels during braking, said slipping being not greater than 17%.

One of the main factors ensuring the safety of aircraft take-off and landing is the ability of the aircraft crews to know the exact value of the maximum coefficient of adhesion which is measured under the conditions most closely approaching the braking conditions of the aircraft wheels, i.e. when the wheels move with a longitudinal slipping of 15-17%.

Known in the prior art are devices for determining the coefficient of adhesion of the pneumatic tyres of transport vehicles to the road pavement.

Thus, a device is known in the form of a passenger car whose frame in the centre of gravity thereof carries longitudinal guides installed on which is a carriage with a measuring wheel.

The car body accommodates a set of measuring instruments with a sensitive element secured to said carriage guides.

On the moving car the measuring wheel can be braked to such an extent that it moves with a slipping ranging from 15% to 100%. For this purpose the device incorporates a disc brake with an independent control comprising a hydraulic system with a servo valve actuated by a sophisticated electronic device.

The normal load applied to the measuring wheel can be adjusted from 0 to 300 kg by means of a pneudraulic jack connected with a nitrogen shock absorber.

Being acted upon by the longitudinal traction force arising on the wheel in the course of braking, the carriage with the measuring wheel moves over its guides and interacts with the sensitive element which thus takes the longitudinal traction force.

The readings of the sensitive element are recorded by the measuring instruments graduated in the units of the coefficient of adhesion with due regard for variations in the normal load.

This device is intended for research purposes since it gives most accurate values of the coefficient of adhesion in comparison with other known devices but on account of complicated design and high cost of the equipment which calls for highly skilled servicing, said device has not become very popular.

Also known in the prior art are simpler devices for determining the coefficient of adhesion. These devices comprise a two-axle trailer whose front axle is connected to a tow pole while the trailer frame between the rear wheels is fitted with a longitudinally movable carriage with a measuring wheel whose diameter is smaller than that of the rear wheels. The measuring wheel is connected with the rear wheels by universal joint shafts.

When the device is in motion, the difference in diameters of the side wheels and of the measuring wheel connected to them, makes the measuring wheel move with longitudinal slipping whose value is governed by the ratio of wheel diameters and is equal to 15%.

In the course of motion of the device, a longitudinal traction force is originated on the measuring wheel, said force displacing the carriage with the measuring wheel along the fore-and-aft axis of the vehicle and compressing the calibrated coil springs.

At the same time the carriage of the measuring wheel acting through a gear-and-rack pair turns the slide of an electric voltage potentiometer which serves as a sensitive element. The changes in the voltage correspond to the value of the longitudinal movement of the carriage which is proportional to the longitudinal traction force arising on the measuring wheel.

Thus, this device measures the longitudinal traction force arising when the measuring wheel moves with a 15% longitudinal slipping. The provision of calibrated coil springs in the measuring chain and a complicated hydraulic-lever shock-absorbing system of the trailer wheels introduces additional errors into measurement of the coefficient of adhesion and calls for highly skilled servicing personnel. Moreover, this device is very heavy (1200 kg) and rather complicated in servicing.

In both above-mentioned devices when the towing vehicle moves irregularly, the carriage moving longitudinally with the measuring wheel develops inertia forces caused by their mass, said forces acting on the sensitive element and thereby increasing the error in measuring the coefficient of adhesion.

Most popular at present is the Swedish "Skidometer" comprising a single-axle trailer whose frame is secured by an articulated tow pole to a towing vehicle and whose wheels are adapted for movement with longitudinal slipping. The device is also provided with a recorder incorporating a sensitive element.

In the latest model of this device the trailer frame is mounted on two supporting wheels and has a third, measuring wheel installed between the supporting wheels and having the same diameter as that of the supporting wheels.

The measuring wheel is connected with the supporting wheels by chain drives with a speed ratio of 1.15 which ensures the movement of the measuring wheel with a longitudinal slipping of 15%.

The rim of the measuring wheel is installed on an intermediate shaft with a provision for rotating. The same shaft carries the sprocket of the chain drive and the sensitive element is installed between the measuring wheel rim and said intermediate shaft with the aid of a flexible mechanism.

When this device is in motion, the longitudinal traction force arising on the measuring wheel creates a brake torque which is converted by the flexible mechanism into an axial force received by the sensitive element.

In the course of this conversion the flexible mechanism can develop an interference which affects the accuracy of determining the value of the coefficient of adhesion.

Furthermore, the provision of the flexible mechanism leads to an unjustified complication and rise in the cost of the device as a whole and calls for uninterrupted skilled servicing in operation.

An object of the present invention resides in providing a device for determining the coefficient of adhesion of pneumatic wheel tyres of transport vehicles to the road pavement which would permit measuring the coefficient of adhesion with a maximum possible accuracy.

Another object of the invention resides in simplifying and cheapening the design of the device as a whole.

Still another object of the invention resides in facilitating the operation of the device and using less skilled operators.

These and other objects are achieved by providing a device for determining the coefficient of adhesion of pneumatic wheel tyres of transport vehicles to the road pavement whose frame is fastened by a tow pole to the towing vehicle and whose wheels are adapted for moving with longitudinal slipping in opposite directions for measuring the coefficient of adhesion and which is provided with a recorder incorporating a sensitive element wherein, according to the invention, the trailer has only two wheels and the sensitive element is located between the trailer frame and the free end of the tow pole and is kinematically linked with them in such a manner that in the course of trailer movement the sensitive element is acted upon by a force which is proportional in magnitude to the sum of absolute values of the longitudinal traction forces acting on the wheels and directed essentially parallel to these forces.

Such a solution allows the coefficient of adhesion to be measured with a maximum possible accuracy because in the course of trailer movement the sensitive element is acted upon by said longitudinal force taken by said element from the trailer frame without any intermediate mechanisms.

When the trailer has only two wheels rotating with slipping in the opposite directions the longitudinal traction forces arising on said wheels and also pointed in opposite directions are transmitted to the trailer frame, creating a torque relative to the trailer centre of gravity in the plane parallel to the road pavement, said torque tending to turn the trailer towards one of the wheels.

Due to the kinematic linkage between the sensitive element and the trailer frame and tow pole, the latter develops a torque which is opposite to said torque and which resists the turning of the trailer.

In this case the sensitive element is acted upon by a longitudinal force whose magnitude is proportional to the longitudinal traction force acting on the wheels. The factor of proportionality is calculated as a ratio of the arms of the location point of the sensitive element and wheel centres of gravity to the centre of gravity of the trailer.

In addition, the location of the sensitive element sideways of the trailer centre of gravity excludes the influence on the sensitive element of the inertia forces arising in the centre of gravity of the trailer during its irregular motion and thereby eliminates the influence of these forces on the value of the coefficient of adhesion, thus improving the accuracy of its measurement.

According to one of the possible embodiments of the present invention, the wheels have different diameters and are arranged symmetrically to the trailer centre of gravity and the sensitive element is articulated to the trailer frame at the point of its intersection with the rolling plane of one of the wheels and its kinematic linkage with the tow pole is effected by a longitudinal rod and a side rod articulated to each other, the free end of the longitudinal rod being articulated to the sensitive element and installed on the trailer frame with a provision for axial motions in the rolling plane of said wheel, essentially parallel to the road pavement, while the free end of the side rod is articulated to the free end of the tow pole.

Owing to the displacement of the longitudinal rod in the rolling plane of one of the wheels parallel to the road pavement, the vector of the longitudinal force of the frame acts on the sensitive element in the direction parallel to the vector of the longitudinal traction force acting on the wheel. In this case the side rod prevents the trailer from turning around its centre of gravity and the tow pole transmits the traction force from the towing vehicle to the trailer frame.

It is practicable that the ends of the longitudinal rod should be installed in guide rollers mounted on the trailer frame.

This will ensure the axial motion of the side rod, essentially parallel to the airfield pavement and the minimum losses for friction in the guides.

The tow pole can be made in the form of a rod articulated to the trailer frame at the point of its intersection with the longitudinal vertical plane passing through the centre of gravity of the trailer.

Such a solution ensures the transmission of the dynamic inertia forces arising in the centre of gravity of the irregularly moving trailer to the frame of the towing vehicle thereby ruling out their effect on the sensitive element.

Now the invention will be described in detail by way of example with reference to the accompanying drawings in which:

FIG. 1 is a schematic general side view of the device according to the invention for determining the coefficient of adhesion of pneumatic wheel tyres of transport vehicles to the road pavement.

FIG. 2 — same, top view with cover removed for convenience;

The device for determining the coefficient of adhesion of pneumatic wheel tyres of transport vehicles to the road pavement is illustrated by describing its embodiment for determining the coefficient of adhesion of the pneumatic wheel tyres of aircraft of the airfield pavement.

Figure 1:
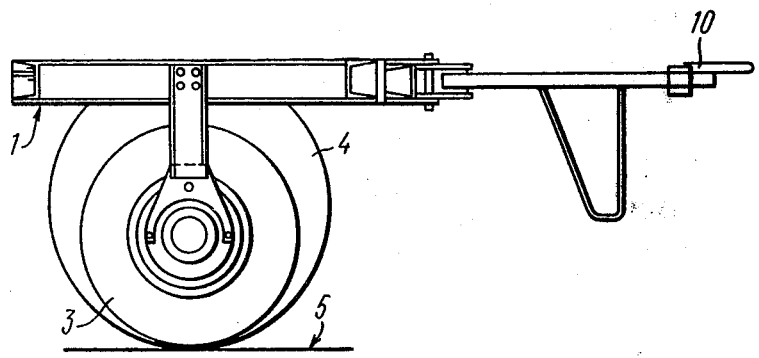

The device for determining the coefficient of adhesion of aircraft wheels to the airfield pavement comprises a two-wheel trailer, whose frame 1 (FIGS. 1 and 2) is secured by an articulated tow pole 2 to the towing vehicle (not shown in the drawing) and is mounted according to the invention only on two wheels 3 and 4 having different diameters and arranged symmetrically relative to the centre of gravity "0" (FIG. 2) of the trailer.

Being of the supporting type, both wheels 3 and 4, are capable of functioning as measuring wheels, too.

Figure 2:
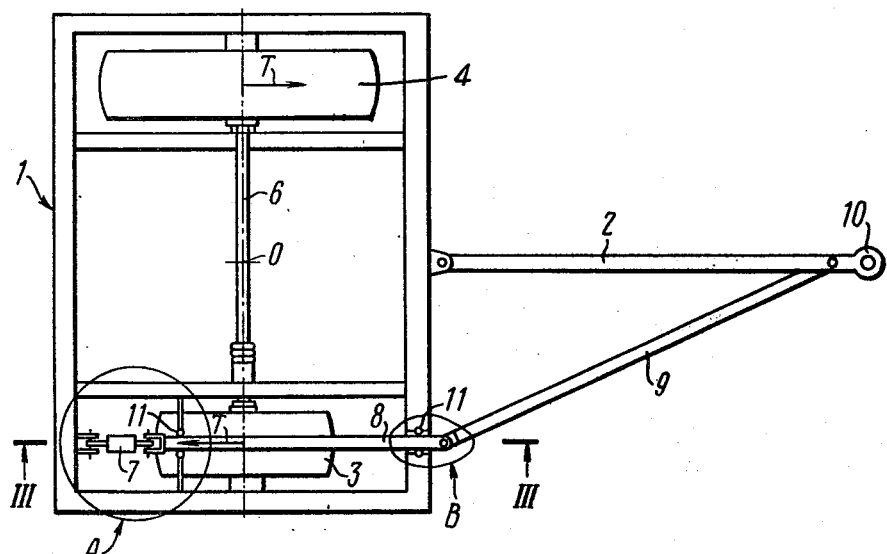

For this purpose the wheels 3 and 4 are adapted for rotation with slipping in the opposite directions while the trailer is driven over the airfield pavement 5. In the trailer according to the present invention this is achieved by interconnecting the wheels 3 and 4 by a universal joint shaft 6 (FIG. 2). The diameters of the wheels 3 and 4 are selected with a ratio of 1.11 to 1.17 which allows their longitudinal slipping of 11-17% at which the magnitude of the adhesion coefficient is, essentially, at a maximum.

The device comprises a recording instrument (not shown in the drawing) installed in the cab of the towing vehicle. The sensitive element 7 (FIG. 2) of this recording instrument is offset from the centre of gravity "0" of the trailer towards the wheel 3 of the smaller diameter and is linked kinematically with the trailer frame 1 and tow pole 2 in such a manner that on the moving trailer the sensitive element 7 is acted upon by a longitudinal force which is proportional in magnitude to the sum of absolute magnitudes of the longitudinal traction forces acting on the wheels 3 and 4.

In the given embodiment of the invention the sensitive element 7 is articulated to the trailer frame 1 at the point where it intersects the rolling plane of the wheel 3 of the smaller diameter.

Figure 3:
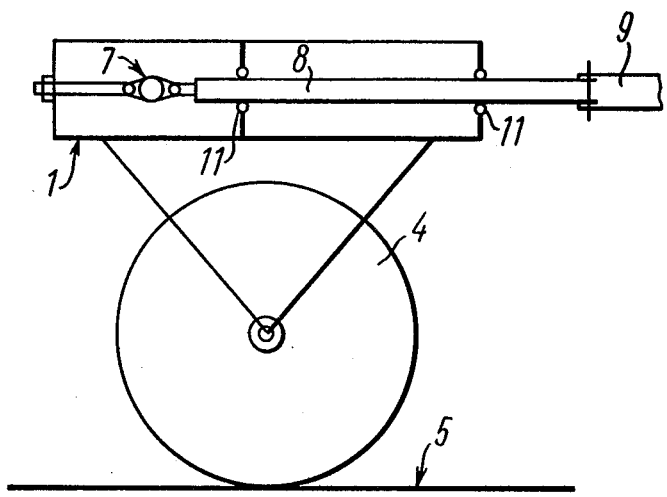
FIG. 3 is a section taken along line III—III in FIG. 2.

The kinematic linkage between the sensitive element 7 and the tow pole 2 consists, according to the invention, of a longitudinal rod 8 and a side rod 9 articulated to each other by their ends. The other end of the longitudinal rod 8 is articulated to the sensitive element 7 and said rod 8 is installed on the trailer frame 1 with a provision for axial motions in the rolling plane of the wheel 3 of the smaller diameter, essentially parallel to the airfield pavement 5 as it is shown in FIG. 3. The free end of the side rod 9 is articulated to the free end of the tow pole 2 which has an eye 10 for coupling to the towing vehicle.

Figure 4:
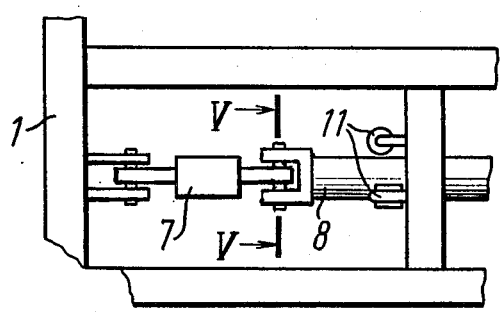
FIG. 4 shows fragment "A" in FIG. 2, enlarged.
Figure 6:
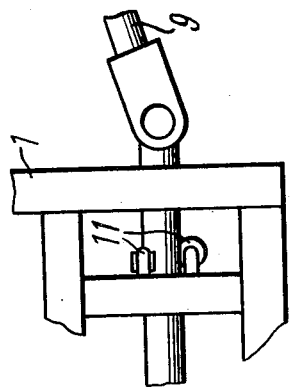
FIG. 6 shows fragment "B" in FIG. 2, enlarged.
Figure 5:
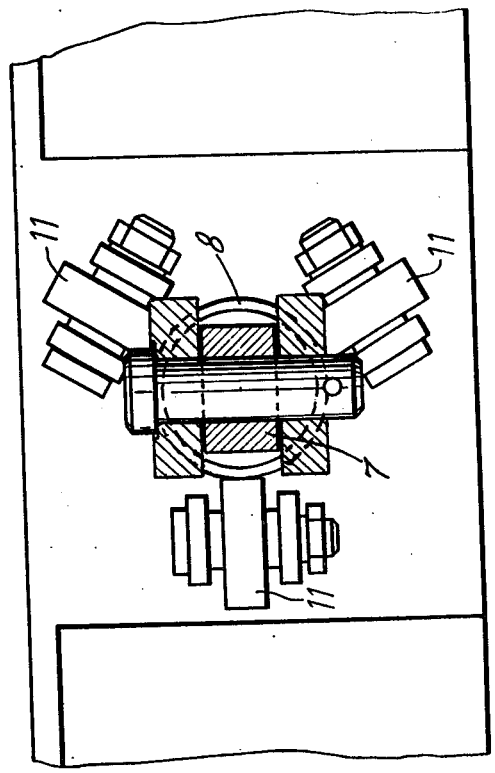
FIG. 5 is a section taken along line V—V in FIG. 4, enlarged.

To provide for the possibility of said axial motions of the longitudinal rod 8, the ends thereof are installed in guide rollers 11 mounted on the trailer frame 1 and arranged in groups of three uniformly around the circumference of the rod 8 for aligning it (as shown in FIGS. 4–6).

The tow pole 2 has the form of a rod one end of which is articulated to the trailer frame 1 at the point where it intersects the longitudinal vertical plane passing through the trailer centre of gravity "0" which rules out the effect of inertia forces arising during irregular motion of the trailer on the accuracy of measuring the coefficient of adhesion by the measuring element.

The sensitive element 7 can be constituted by an extension type strain gauge.

The device for determining the coefficient of adhesion of pneumatic wheel tyres to the airfield pavement functions as follows.

As the device is being towed by a motor truck, the trailer wheels 3 and 4 rotate with longitudinal slipping in opposite directions because said wheels are interconnected by a universal joint shaft 6. The ratio of diameters of the wheels 3 and 4 (1.11–1.17) ensures their slipping at which the coefficient of adhesion is at a maximum.

At the moment of slipping the wheels 3 and 4 at the point of their contact with the airfield pavement develop maximum longitudinal traction forces T (FIG. 2) pointing in opposite directions; said forces are transmitted to the trailer frame 1 and create a torque relative to the trailer centre of gravity "0", said torque tending to turn the trailer towards the wheel 3 of the smaller diameter. This turning torque is resisted by the towing vehicle which is coupled to the trailer frame 1 by the side rod 9, longitudinal rod 8 and the sensitive element 7 which receives the longitudinal force from the longitudinal rod 8, said force being equal in magnitude to the sum of longitudinal traction forces T acting on the wheels 3 and 4.

The longitudinal force acting on the sensitive element 7 is transformed into an electric signal which is transmitted to the recording element installed in the cab of the towing vehicle and graduated in the units of the coefficient of adhesion of the trailer wheels 3 and 4 to the airfield pavement 5.

What is claimed is:

1. A device for determining the coefficient of adhesion of wheel tires of transport vehicles to a road pavement comprising: a single-axle trailer having a frame, said frame having two wheels on which said frame is mounted and which are adapted for rotating in the course of movement of said trailer with longitudinal slipping in opposite directions; a tow pole articulated to said frame for coupling it to a towing vehicle; a recording instrument with a sensitive element located between the frame and the free end of the trailer tow pole and linked kinematically with said frame and pole in such a manner that when the trailer is moved said sensitive element is acted upon by a force which is proportional in magnitude to the sum of absolute values of the longitudinal traction forces acting on the wheels of said trailer and which is directed, essentially, parallel to said forces, the wheels of said trailer having different diameters and being arranged symmetrically relative to the trailer centre of gravity, the sensitive element being articulated to the trailer frame at the point where it intersects the rolling plane of one of the wheels; and means for kinematically linking said sensitive element with the tow pole and comprising longitudinal and side rods articulated to each other so that a free end of the longitudinal rod is articulated to the sensitive element and is installed on the trailer frame with a provision for axial motions in the rolling plane of said wheel, essentially parallel to the road pavement, while a free end of the side rod is articulated to the free end of the tow pole.

2. A device as claimed in claim 1 wherein the ends of the longitudinal rod are installed in guide rollers mounted on the trailer frame.

3. A device as claimed in claim 1 wherein the tow pole has the form of a rod one end of which is articulated to the trailer frame at the point where it intersects the longitudinal vertical plane passing through the trailer centre of gravity.

* * * * *